(12) United States Patent
Osterbauer et al.

(10) Patent No.: US 11,701,491 B2
(45) Date of Patent: Jul. 18, 2023

(54) DEFLECTABLE TORQUE CABLE FOR DELIVERY OF MEDICAL DEVICES

(71) Applicant: St. Jude Medical, Cardiology Division, Inc., St. Paul, MN (US)

(72) Inventors: Philip Osterbauer, Wyoming, MN (US); Brian Perszyk, Shoreview, MN (US); Michael P. Meyer, Minnetrista, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 17 days.

(21) Appl. No.: 17/003,359

(22) Filed: Aug. 26, 2020

(65) Prior Publication Data

US 2021/0060295 A1 Mar. 4, 2021

Related U.S. Application Data

(60) Provisional application No. 62/942,286, filed on Dec. 2, 2019, provisional application No. 62/892,525, filed on Aug. 27, 2019.

(51) Int. Cl.
*A61M 25/01* (2006.01)
*A61B 17/12* (2006.01)
*A61B 17/00* (2006.01)

(52) U.S. Cl.
CPC ... *A61M 25/0105* (2013.01); *A61B 17/12122* (2013.01); *A61B 2017/00323* (2013.01);
(Continued)

(58) Field of Classification Search
CPC ...... A61M 25/0105; A61M 2025/1054; A61B 17/12122; A61B 17/0057; A61B 17/12022; A61B 17/12136; A61B 2017/00323; A61B 2017/1205; A61B 2017/00526; A61B 2017/00243; A61B 2017/00606; A61B 2017/00575; A61B 2017/00623;
(Continued)

(56) References Cited

U.S. PATENT DOCUMENTS 6,179,809 B1 1/2001 Khairkhahan et al.
10,758,241 B1 * 9/2020 Lashinski ........ A61B 17/12168
(Continued)

FOREIGN PATENT DOCUMENTS

WO 2017062514 A1 4/2017
WO 2017223053 A1 12/2017
(Continued)

OTHER PUBLICATIONS

European Search Report for corresponding EP Patent Application No. 20192946.0, dated May 21, 2021, 8 pp.

*Primary Examiner* — Martin T Ton
(74) *Attorney, Agent, or Firm* — Armstrong Teasdale LLP (57) ABSTRACT

A delivery cable for delivering a medical device and a delivery device including the same are described herein. The delivery cable includes a flexible inner core, an outer coil surrounding at least a portion of the flexible inner core, and a pull wire disposed between the flexible inner core and the outer coil, the pull wire configured to deflect a distal deflectable portion of the delivery cable upon manipulation thereof. Methods of making the delivery cable and methods of using the delivery cable to deploy a medical device are also described herein.

17 Claims, 7 Drawing Sheets

(52) U.S. Cl.
CPC ............... *A61B 2017/00526* (2013.01); *A61B 2017/1205* (2013.01)

(58) Field of Classification Search
CPC .......... A61B 2017/00845; A61B 2017/12095; A61B 2017/00389; A61B 2090/376; A61B 2090/3966
USPC ......................................................... 606/108
See application file for complete search history.

(56) References Cited

U.S. PATENT DOCUMENTS

| | | | | |
|---|---|---|---|---|
| 2002/0072737 | A1* | 6/2002 | Belden | A61N 1/0563 606/34 |
| 2003/0125726 | A1* | 7/2003 | Maguire | A61N 7/02 606/41 |
| 2005/0119615 | A1* | 6/2005 | Noriega | A61M 25/09 604/95.04 |
| 2007/0203562 | A1* | 8/2007 | Malewicz | A61M 25/1011 623/1.34 |
| 2012/0010490 | A1 | 1/2012 | Kauphusman et al. | |
| 2016/0022961 | A1* | 1/2016 | Rosenman | A61M 25/0141 604/95.04 |
| 2018/0296801 | A1* | 10/2018 | Tegg | A61M 25/0147 |
| 2019/0110796 | A1* | 4/2019 | Jayaraman | A61B 17/12168 |
| 2019/0183512 | A1* | 6/2019 | Subramaniam | A61B 17/12027 |
| 2019/0192820 | A1* | 6/2019 | Olson | A61M 25/0136 |
| 2019/0274668 | A1* | 9/2019 | Glimsdale | A61B 17/0057 |
| 2020/0222034 | A1* | 7/2020 | Liu | A61B 17/12022 |
| 2021/0059685 | A1* | 3/2021 | Groff | A61B 17/12122 |

FOREIGN PATENT DOCUMENTS

| | | | | |
|---|---|---|---|---|
| WO | | 2018195162 A1 | 10/2018 | |
| WO | WO-2019099896 A1 | * | 5/2019 | ....... A61B 17/12168 |

* cited by examiner

DEFLECTABLE TORQUE CABLE FOR DELIVERY OF MEDICAL DEVICES

CROSS-REFERENCE TO RELATED APPLICATIONS

The present application claims the benefit of priority to U.S. Provisional Patent Application No. 62/892,525, filed Aug. 27, 2019, and to U.S. Provisional Patent Application No. 62/942,286, filed Dec. 2, 2019, the entire contents of which are hereby incorporated by reference herein.

BACKGROUND OF THE DISCLOSURE a. Field of Disclosure

The present disclosure generally relates to a medical device delivery cable and methods of making and using the same. In particular, the present disclosure relates to a medical device delivery cable including a flexible inner member, an outer member, and a pull wire disposed between the inner member and the outer member to deflect a deflectable portion of the delivery cable. Methods of manufacturing and using the medical device delivery cables are also disclosed.

b. Background Art

Delivery devices including, among other components, catheters and delivery cables are used for an ever-growing number of procedures, and in particular, for the delivery of medical devices to a target site. Typically, the catheter is manipulated through the patient's vasculature and to the intended site, for example, a site within the patient's heart or other organ and the delivery cable is used to advance the medical device through the catheter and to the target site. Once the medical device has reached the target site, the delivery cable may be detached or uncoupled from the medical device such that the medical device is deployed from both the catheter and the delivery cable.

Generally, the catheter would have an overall outside diameter small enough to negotiate blood vessels or other anatomy while retaining an inner diameter ("bore size") large enough to accommodate the medical device (and delivery cable) therethrough. Because the path within the patient may be long, tortuous, and/or involve intricate placement of a medical device(s), maneuverability via steering the catheter may be particularly beneficial.

In addition, it would be desirable for the delivery cable to be deflectable to enable additional maneuverability of the medical device coupled thereto. It has been contemplated to couple a pull wire to a delivery sheath, which enables deflection of the delivery sheath. However, such an arrangement reduces a usable inner diameter of the delivery sheath, which limits the outer diameter of delivery cables and medical devices that can be delivered through such a delivery sheath.

SUMMARY OF THE DISCLOSURE

In one aspect of the present disclosure, a delivery cable is provided. The delivery cable includes a flexible inner core, an outer coil surrounding at least a portion of the flexible inner core, and a pull wire disposed between the flexible inner core and the outer coil. The pull wire is configured to deflect a distal deflectable portion of the delivery cable upon manipulation thereof.

In another aspect, a delivery device for delivering a medical device to a target site is provided. The delivery device includes an outer sheath, and a delivery cable positioned within the outer sheath and movable along a longitudinal axis with respect to the outer sheath. The delivery cable includes a flexible inner core, an outer coil surrounding at least a portion of the flexible inner core, and a pull wire disposed between the flexible inner core and the outer coil. The pull wire is configured to deflect a distal deflectable portion of the delivery cable upon manipulation thereof.

In a further aspect, a method for implanting a medical device at a target site in a subject using a delivery cable and a delivery sheath is provided. The method includes deploying the delivery sheath into the subject, and advancing the delivery cable through the deployed delivery sheath. The delivery cable includes a flexible inner core, an outer coil surrounding at least a portion of the flexible inner core, and a pull wire disposed between the flexible inner core and the outer coil. The method also includes deflecting a distal deflectable portion of the delivery cable by manipulating the pull wire, and deploying the medical device at the target site by detaching the medical device from the delivery cable.

In yet another aspect, a method of manufacturing a delivery cable is provided. The method includes providing a flexible inner core, inserting the flexible inner core at least partially into an outer coil, inserting a pull wire between the flexible inner core and the outer coil, and coupling the pull wire to the outer coil.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Septal occluders or other collapsible medical devices may be delivered through a catheter or delivery sheath and to a target site using a delivery cable. However, the collapsible medical device may not be precisely located at the target site, such that the delivery cable may need to be withdrawn, repositioned, adjusted, and the like, in order to properly position the collapsible medical device. Accordingly, the present disclosure is directed to a delivery cable including a distal deflectable portion that is deflectable using an internal pull wire.

The delivery cable includes a flexible inner member, or core, and an outer member, or coil. A pull wire is disposed between the outer coil and the flexible inner member. Manipulation of the pull wire causes the distal deflectable portion of the delivery cable to deflect, which may enhance positioning of a medical device coupled to the delivery cable at a target location.

The delivery cable also includes an endscrew coupled to a distal end of the delivery cable and configured to engage with a medical device to be delivered using the delivery cable. In one example embodiment, the endscrew is threaded to the medical device. Accordingly, to release the medical device at the target location, the endscrew must be rotated to disengage with the medical device. However, the delivery cable cannot be rotated while the distal deflectable portion is deflected without undesirably displacing the medical device. Therefore, the flexible inner core is rotatable, which enables rotation of the endscrew without displacement thereof. The delivery cable further includes a bushing to provide a bearing interface between the endscrew and the outer coil.

Additionally, a steerable delivery cable as described herein may provide an additional plane of deflection when combined with a steerable sheath. Moreover, the steerable delivery cable may be used to optimize alignment of a proximal end of the medical device prior to release.

Figure 1:
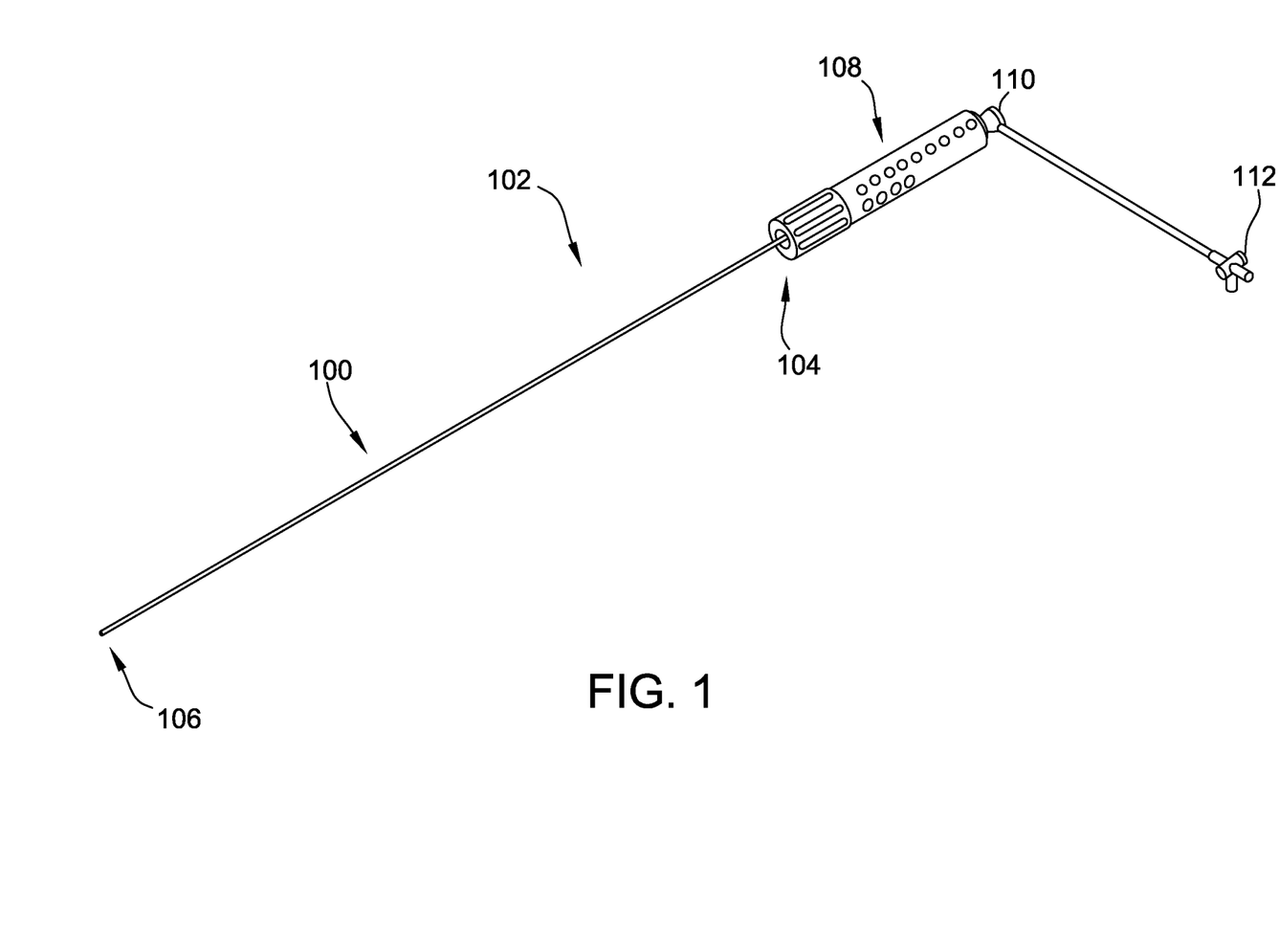
FIG. 1 is a perspective view of one embodiment of an introducer or catheter assembly in which the principles described herein may be implemented.

Referring now to the Figures, FIG. 1 is a perspective view of a catheter assembly or introducer assembly 102 according to one embodiment including a catheter or an introducer 100 having a proximal portion 104 and a distal portion 106. The introducer 100 may be operably connected to a handle assembly 108, which assists in guiding or steering the introducer 100 during procedures. The introducer assembly 102 further includes a hub 110 operably connected to an inner lumen (not shown) within the handle assembly 108 for insertion or delivery of catheter assemblies, fluids, or any other devices known to those of ordinary skill in the art. Optionally, introducer assembly 102 further includes a valve 112 operably connected to hub 110.

Figure 2:
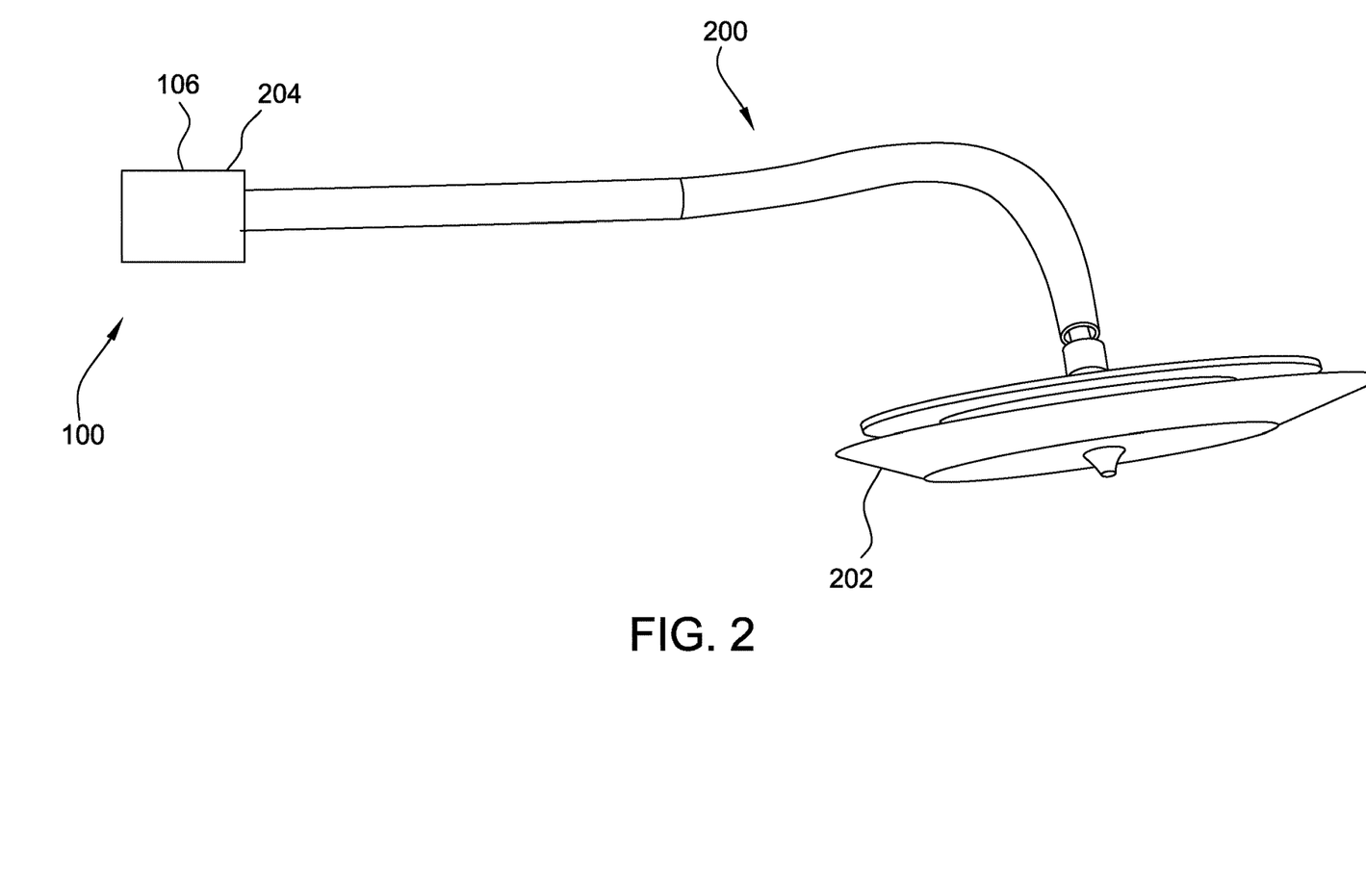
FIG. 2 is a schematic diagram of a portion of the assembly shown in FIG. 1 in combination with one embodiment of a delivery cable and a medical device.

FIG. 2 is a schematic diagram of a portion of the introducer 100 shown in FIG. 1 in combination with one embodiment of a delivery cable 200 and a medical device 202. As shown in FIG. 2, the delivery cable 200 extends from the distal portion 106 of the introducer 100 (i.e., a delivery sheath 204 of the introducer 100), and is coupled to the medical device 202. In this embodiment, the medical device 202 is a collapsible occluder. Alternatively, the medical device 202 may be any device capable of being coupled to the delivery cable 200.

Figure 3:
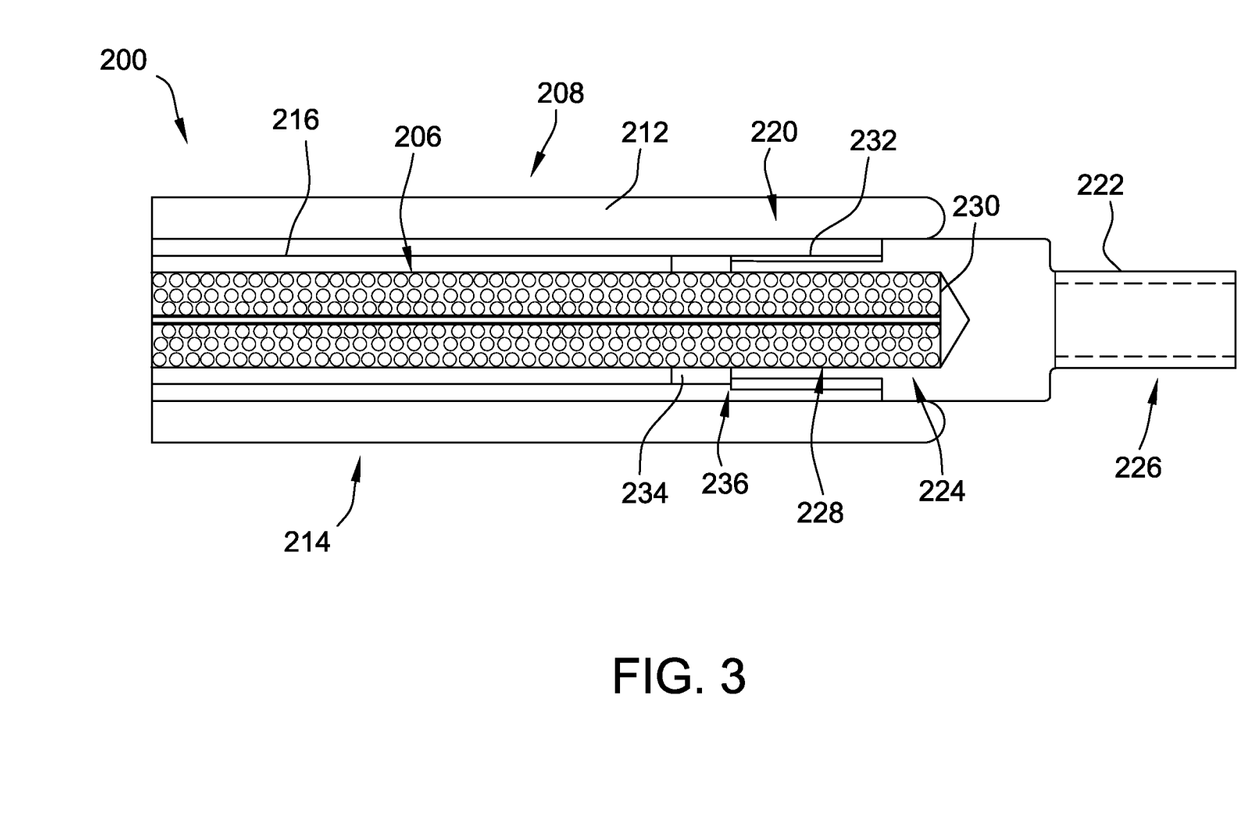
FIG. 3 is a longitudinal cross-sectional view of the delivery cable shown in FIG. 2.

FIG. 3 is a longitudinal cross-sectional view of the delivery cable 200. The delivery cable 200 may be used to facilitate delivering a medical device (e.g., the medical device 202, shown in FIG. 2) such as, but not limited to, a collapsible occluder or the like. It should be noted that although the delivery cable 200 is described herein as being useful in combination with the introducer 100 illustrated in FIGS. 1 and 2, the delivery cable 200 may be used in the delivery process of many various medical devices and in combination with many various sheaths, loaders, valves, etc.

As shown in FIG. 3, the delivery cable 200 includes a flexible inner member (also referred to herein as a flexible core) 206. The delivery cable 200 has a distal section 208 and a proximal section 210 (see FIGS. 4 and 5). At least a portion of the inner member 206 is surrounded by an outer member or outer coil 212 at least at the distal section 208. In some embodiments, at least a portion of the inner member 206 is also surrounded by the outer coil 212 at the proximal section 210 thereof. In the example embodiment, the distal section 208 includes a distal deflectable portion 214 (see also FIGS. 4 and 5).

The delivery cable 200 further includes a pull wire 216 disposed between the inner member 206 and the outer coil 212. The pull wire 216 extends longitudinally through the delivery cable 200, between the inner member 206 and the outer coil 212, from the proximal section 210 to the distal section 208. In the example embodiment, the pull wire 216 is coupled (directly or indirectly) to the outer coil 212. In particular, the pull wire 216 is coupled to the outer coil 212 at a distal end 220 thereof, within the distal deflectable portion 214 of the delivery cable 200. Upon manipulation of the pull wire 216, as described further herein, the pull wire 216 causes deflection of the outer coil 212, which causes deflection of the distal deflectable portion 214. Although not shown, in some embodiments, the pull wire 216 includes a coating or jacket provided on an outer surface thereof. The jacket may be a polymer jacket that reduces friction between the pull wire 216 and adjacent components (e.g., an inner surface of the outer coil 212 and/or an outer surface of the inner member 206).

An endscrew 222 is coupled to a distal end 224 of the inner member 206 to facilitate selectively attaching and detaching a medical device (e.g., the medical device 202, shown in FIG. 2) to the delivery cable 200. In the example embodiment, the endscrew 222 includes a threaded portion 226 configured to cooperate with a corresponding threaded portion (not shown) positioned on or within the medical device to be delivered, such that the medical device may be engaged or disengaged (i.e., coupled to or released from) the delivery cable 200 upon rotation of the endscrew 222.

The endscrew 222 is attached to the inner member 206 via any method suitable to sufficiently secure the endscrew 222 to the inner member 206. For example, suitable methods include, but are not limited to, bonding via an adhesive (such as an epoxy), connecting (e.g., using a coupling member, such as a stainless steel tube or platinum-iridium marker band that is dome welded to a distal end of the inner member 206 prior to being crimp or spot welded to the endscrew 222), soldering, welding, spot welding or crimp welding, clamping, swaging, crimping, or any combination thereof. In the illustrated embodiment, a proximal portion 228 of the endscrew 222 is coupled to the distal end 224 of the inner member 206. More specifically, the proximal portion 228 includes a pocket 230 formed therein that receives the distal end 224 of the inner member 206 therein. As described above, the inner member 206 may be adhered, welded, and/or otherwise coupled within the pocket 230.

In other embodiments, the endscrew 222 and the inner member 206 may also be integrally formed (e.g., an overmolded screw). In still other embodiments, as an alternative to the endscrew 222, any suitable device for attaching and detaching a medical device may be used.

Figure 4:
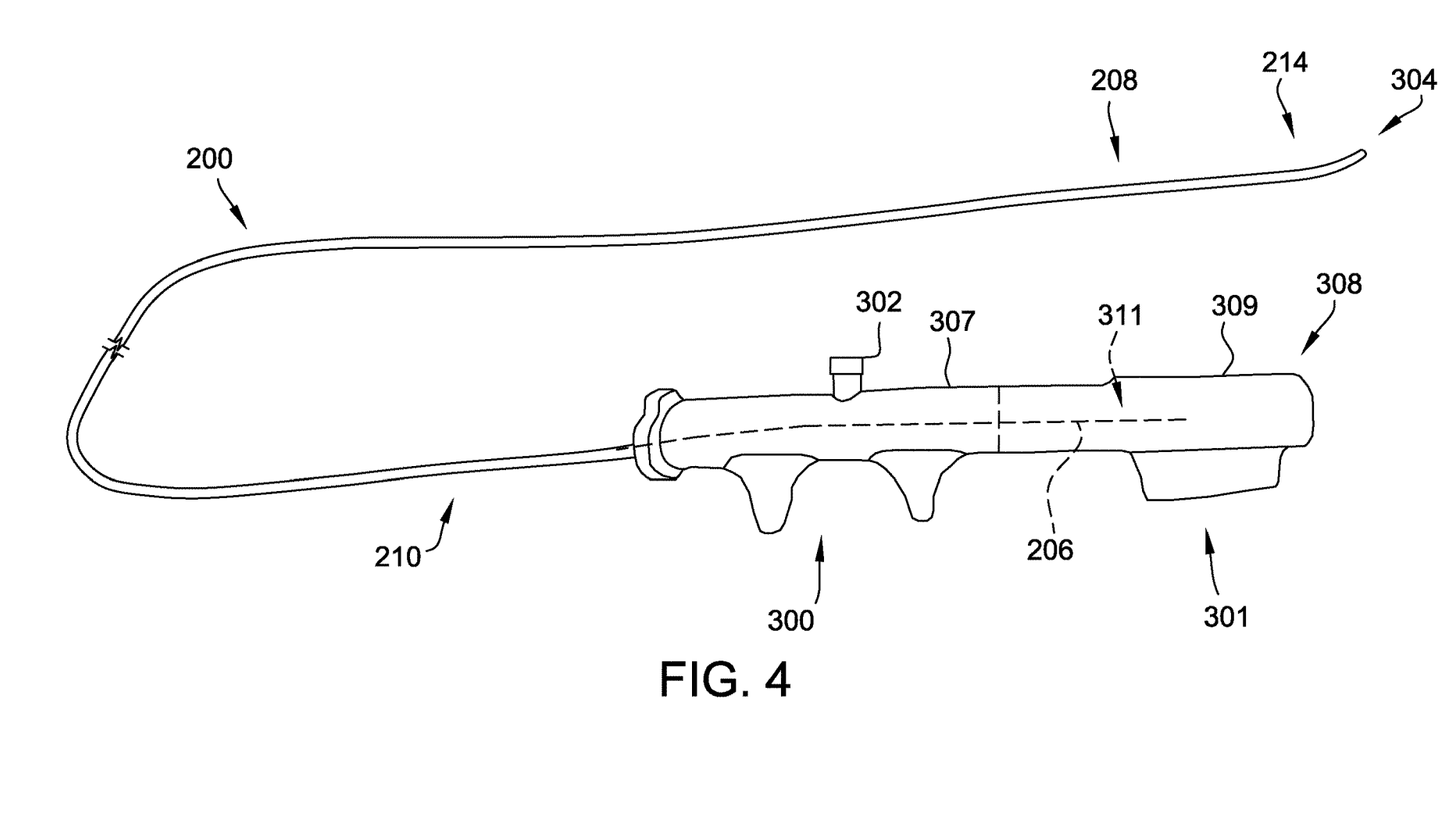
FIG. 4 is perspective view of the delivery cable shown in FIGS. 2 and 3 with a distal deflectable portion thereof in a first, non-deflected orientation.
Figure 5:
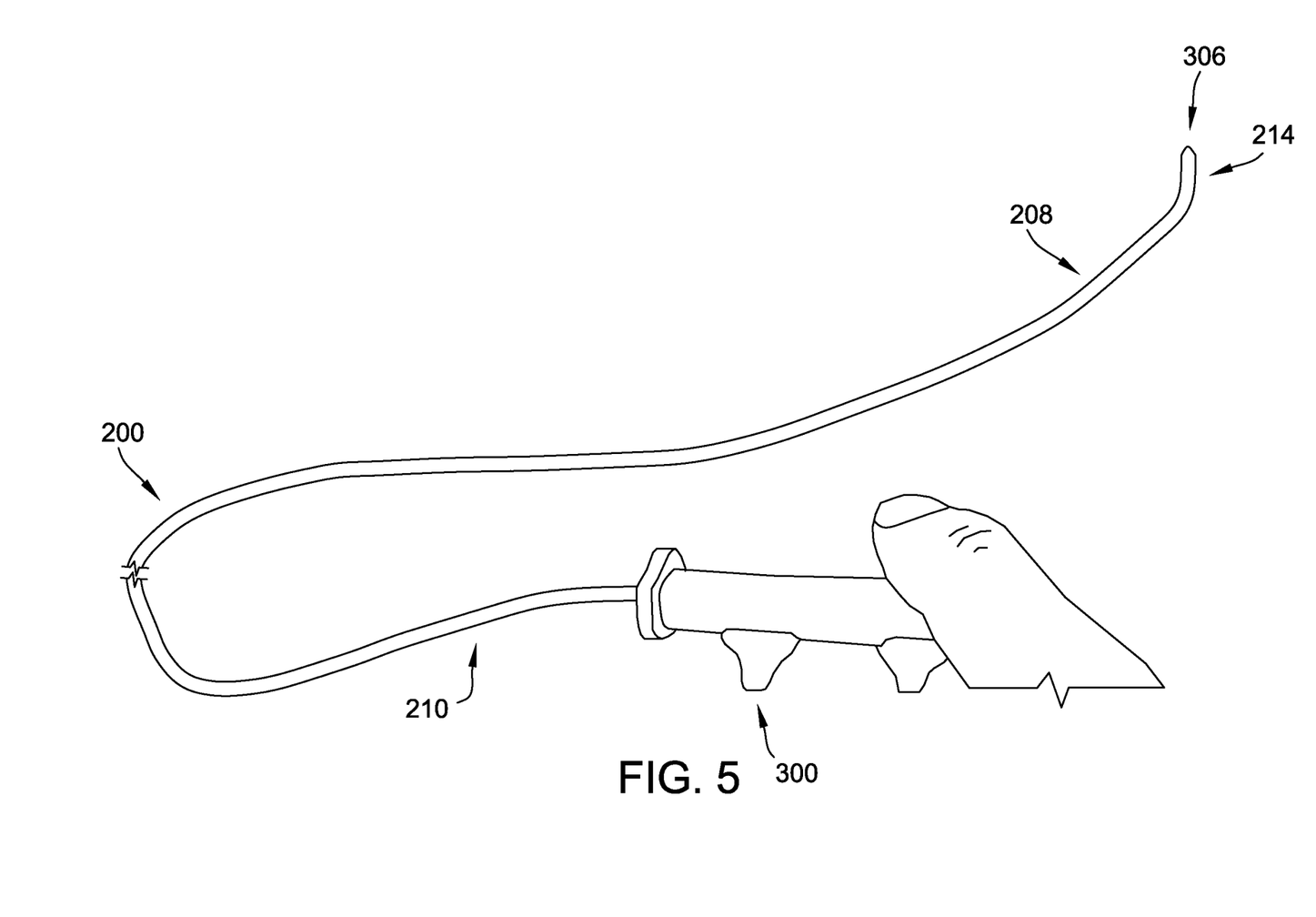
FIG. 5 is a perspective view of the delivery cable shown in FIGS. 2 and 3 with the distal deflectable portion thereof in a second, deflected orientation.

Turning now to FIGS. 4 and 5, deflection of the distal deflectable portion 214 of the delivery cable 200 is illustrated. In the example embodiment, a handle assembly 300 is coupled to the proximal section 210 of the delivery cable 200. The handle assembly 300 may be integral to the handle assembly 108 of the introducer assembly 102, or may be separate therefrom. The handle assembly 300 includes a grip member 301 including at least one deflection control 302 that, upon manipulation thereof, causes deflection of the distal deflectable portion 214 from a first, non-deflected position 304 (see FIG. 4) to a second, deflected position 306 (see FIG. 5), and vice versa. The deflection control 302 may include a knob, a lever, a button, and/or any suitable control that may be manipulated by a physician.

In particular, the deflection control 302 is coupled to a proximal end (not shown) of the pull wire 216. Manipulation of the deflection control 302 increases tension in the pull wire 216, which causes the distal end of the pull wire 216 to exert a pulling force on the outer coil 212 (and, therefore, on the distal deflectable portion 214 of the delivery cable 200). This pulling force causes deflection of the outer coil 212, and, therefore, deflection of the distal deflectable portion 214 of the delivery cable 200. Deflection of the delivery cable 200 may enhance the ability of a physician to accurately and precisely locate a medical device (e.g., an occluder) at a target location.

Opposite or subsequent manipulation of the deflection control 302 reduces tension in the pull wire 216, which causes the pull wire 216 to reduce the force exerted on the outer coil 212. In turn, the outer coil 212 straightens.

When the distal deflectable portion 214 is in the second, deflected position 306, the endscrew 222 is oriented at an oblique angle with respect to a longitudinal axis of the delivery cable 200. Accordingly, any rotation of the delivery cable 200 while the distal deflectable portion 214 is deflected would result in an elliptical movement of the endscrew 222. Such movement may be undesirable, as such movement would also move any medical device coupled to the endscrew 222 in a corresponding path. That is, the medical device would be displaced from its proper position at the target location. However, where the endscrew 222 is threadably engaged with the medical device, the endscrew 222 must be rotated to disengage the endscrew 222 from medical device (i.e., to deploy the medical device at the target location).

Therefore, in the example embodiment, the inner member 206, to which the endscrew 222 is coupled, is rotatable within the outer coil 212. Rotation of the inner member 206, but not the outer coil 212, enables rotation of the endscrew 222 without elliptical movement thereof. Accordingly, rotating the inner member 206 enables disengagement of the endscrew 222 from the medical device. In some embodiments, the handle assembly 300 further includes a rotation control 308 that, upon manipulation thereof, causes rotation of the inner member 206 within the outer coil 212. The rotation control 308 may include a knob, a rotatable flange, a lever, and/or any other suitable control. In the illustrated embodiment, the rotation control 308 is embodied as a rotatable portion 309 of the handle assembly 300. Specifically, the grip member 301 is split into a fixed or non-rotatable portion 307 and a rotatable portion 309. A proximal end 311 of the inner member 206 is housed or fixed within the rotatable portion 309 of the grip member 301. Rotation of the rotational portion 309 (i.e., the rotation control 308) causes rotation of the inner member 206.

Returning to FIG. 3, the delivery cable 200 further includes a bushing 232 disposed between the outer coil 212 and the endscrew 222, particularly the proximal portion 228 thereof. The bushing 232 provides a bearing interface between the endscrew 222 and the outer coil 212 during rotation of the inner member 206 and the endscrew 222 (e.g., to reduce friction between the endscrew 222 and the outer coil 212). In the embodiment of FIG. 3, the bushing 232 is embodied as a sleeve surrounding the proximal portion 228 of the endscrew 222. In at least some embodiments, the bushing 232 is embodied as a cylindrical sleeve including a longitudinal slit (not shown) in a cylindrical sidewall thereof. Alternatively, the bushing 232 is a continuous, unbroken cylindrical sleeve. In other embodiments, the bushing 232 may be any other suitable bearing component. The bushing 232 may be coupled (e.g., welded, adhered, etc.) to the pull wire 216 and/or to the outer coil 212. In the exemplary embodiment, the pull wire 216 is coupled to the outer coil 212 via the bushing 232. More specifically, the pull wire 216 is coupled to the bushing, and the outer coil 212 is coupled to the bushing 232. As described above, however, the outer coil 212 may additionally or alternatively be (directly) coupled to the pull wire 216.

In addition, the delivery cable 200 includes a proximal disc 234 coupled to a proximal end 236 of the endscrew 222. The proximal disc 234 is positioned proximally of the bushing 232 and is configured to prevent longitudinal translation of the bushing 232 within the outer coil 212. The proximal disc 234 may be welded, adhered, molded, and/or otherwise coupled to the proximal end 236 of the endscrew 222. Moreover, in the exemplary embodiment, the bushing 232 is extended over at least a portion of the proximal disc 234. Specifically, after the proximal disc 234 is coupled to the endscrew 222, the bushing 232 is slid over the endscrew 222 and extended over at least a portion of the proximal disc 234. In at least some embodiments, the bushing 232 may expand to accommodate the proximal disc 234 therein (e.g., where the bushing 232 is formed with a longitudinal slit). In some embodiments, a proximal surface of the proximal disc 234 may be curved or chamfered, which may facilitate extending the bushing 232 thereover with less force.

The inner member 206 is formed of any material and has any configuration suitable to provide both torque strength and flexibility to the delivery cable 200 and enables the delivery cable 200 to function or operate as described herein. For example, the inner member 206 may be configured so as to optimize torque strength and/or flexibility by modifying a length of the inner member 206, a diameter or number of wires that may form the inner member 206, a number of layers forming the inner member 206, and/or the winding direction for each such layer.

The outer coil 212 may be sized and configured so as to provide sufficient column strength to the delivery cable 200 to assist in delivering the medical device through a catheter or delivery sheath. Additionally or alternatively, the outer coil 212 may be sized and configured to provide sufficient flexibility to the delivery cable 200 to prevent the tendency of the medical device being delivered via the delivery cable 200 to move, "jump," pull, or bias upon detaching the medical device from the delivery cable 200 and to prevent undesired straightening of a delivery sheath during delivery of a medical device. Additionally or alternatively, the outer coil 212 may be further sized and configured so as to reduce the ability or tendency of the delivery cable 200, and in particular the distal section 208 thereof, to "snake," curve, or bunch within the catheter or delivery sheath. For example, the outer coil 212 may have an outer diameter that is slightly smaller than an inner diameter of a catheter or delivery sheath through which the delivery cable 200 is advanced during delivery of a medical device. By keeping the space between the catheter or delivery sheath and the outer surface of the outer coil 212 minimized, the ability of the outer coil 212 to "snake," bunch, or curve within a catheter or delivery sheath during advancement of the delivery cable 200 therethrough is reduced, which in turn, reduces the amount of force required to advance a medical device through the catheter or delivery sheath.

The outer coil 212 may be formed of any number of wires, having any size and shape, and arranged in any configuration suitable to provide the desired flexibility and/or strength of the outer coil 212. As will be understood by those of skill in the art, the size, shape, diameter, and/or material of the outer coil 212 may be modified without departing from the scope of the disclosure. For example, the outer coil 212 may be nitinol in some embodiments.

The pull wire 216 may be formed from one or more wires of any suitable material, and may have any size or gauge suitable to induce deflection of the distal deflectable portion 214 of the delivery cable. The pull wire 216 may be formed from, for example, thermoplastic materials, platinum, steel, tantalum, nickel, tungsten, alloys thereof, and/or any other suitable material. Additionally, the pull wire 216 may be coated with and/or encased in, for example, nylon, PVC, thermoplastic elastomer (TPE), and/or other suitable coating(s) or jacket(s) to reduce friction between the pull wire 216 and adjacent components of the delivery cable 200. Moreover, the pull wire 216 may be round or flat or may have any other shape to optimize mechanical properties thereof and/or to ensure an optimal fit within the delivery cable 200. The pull wire 216 may be a pull-pull wire, a push-pull wire, and/or may include multiple pull wires.

It should be readily understood that the delivery cable 200 may include a material positioned over at least a portion of the outer coil 212 to reduce the amount of air ingress during advancement of the medical device through a catheter or other delivery device and/or to increase the lubriciousness of the delivery cable 200 thus aiding in a smoother advancement of the delivery cable 200 through a patient's vasculature. In one embodiment, at least a portion of the outer surface of the outer coil 212, and in some embodiments an entire outer surface of the outer coil 212, is coated, sealed, or surrounded by a heat shrink material (not shown) suitable to reduce or prevent air ingress during advancement of the medical device during delivery thereof.

Figure 6:
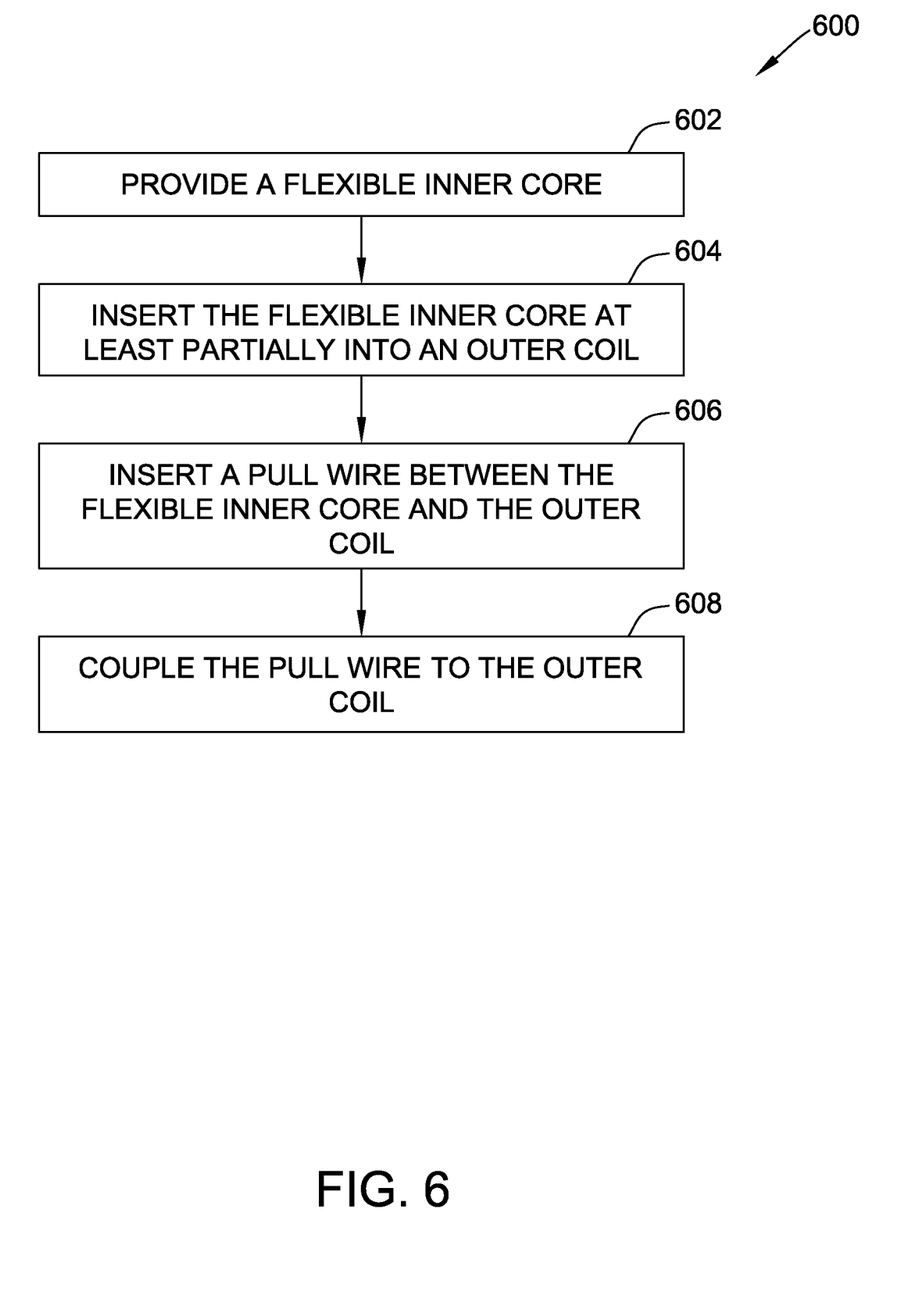
FIG. 6 is a flow diagram of a method of manufacturing a delivery cable according to one embodiment.

FIG. 6 is a flow diagram of a method 600 for manufacturing a delivery cable, such as the delivery cable 200 (shown in FIG. 3), according to one embodiment. Notably, the steps in method 600 may be performed in any suitable order, and are not limited to being performed in the order shown in FIG. 6.

Method 600 includes providing 602 a flexible inner core (e.g., the inner member 206) and inserting 604 the flexible inner core at least partially into an outer coil (e.g., the outer coil 212, both shown in FIG. 3). Method 600 also includes inserting 606 a pull wire (e.g., the pull wire 216, also shown in FIG. 3) between the flexible inner core and the outer coil, and coupling 608 the pull wire to the outer coil.

In some embodiments, method 600 further includes coupling an endscrew (e.g., the endscrew 222, shown in FIG. 3) to a distal end of the flexible inner core. The endscrew may be coupled to the flexible inner core via crimping. In some such embodiments, method 600 also includes coupling a bushing (e.g., the bushing 232, also shown in FIG. 3) to the flexible inner core between a proximal portion of the endscrew and the outer coil to provide a bearing interface between the endscrew and the outer coil. In some such embodiments, coupling 608 includes coupling the pull wire to the outer coil via the bushing, by coupling (e.g., welding) the pull wire to the bushing, and coupling (e.g., welding) the bushing to the outer coil.

In further embodiments, method 600 may include coupling a proximal disc (e.g., the proximal disc 234, also shown in FIG. 3) to a proximal end of the endscrew, the proximal disc configured to prevent proximal translation of the bushing within the outer coil. The proximal disc may be coupled to the endscrew via welding, and this coupling may be performed prior to coupling the bushing to the flexible inner core.

Additionally, method 600 may include coupling a handle assembly (e.g., the handle assembly 300) to a proximal end of the delivery cable, wherein the handle assembly includes a rotation control (e.g., the rotation control 308, both shown in FIG. 4), and coupling a proximal end of the flexible inner core to the rotation control.

Additionally or alternatively, method 600 may include coupling a handle assembly to a proximal end of the delivery cable, wherein the handle assembly includes a deflection control (e.g., the deflection control 302, also shown in FIG. 4), and coupling a proximal end of the pull wire to the deflection control.

Figure 7:
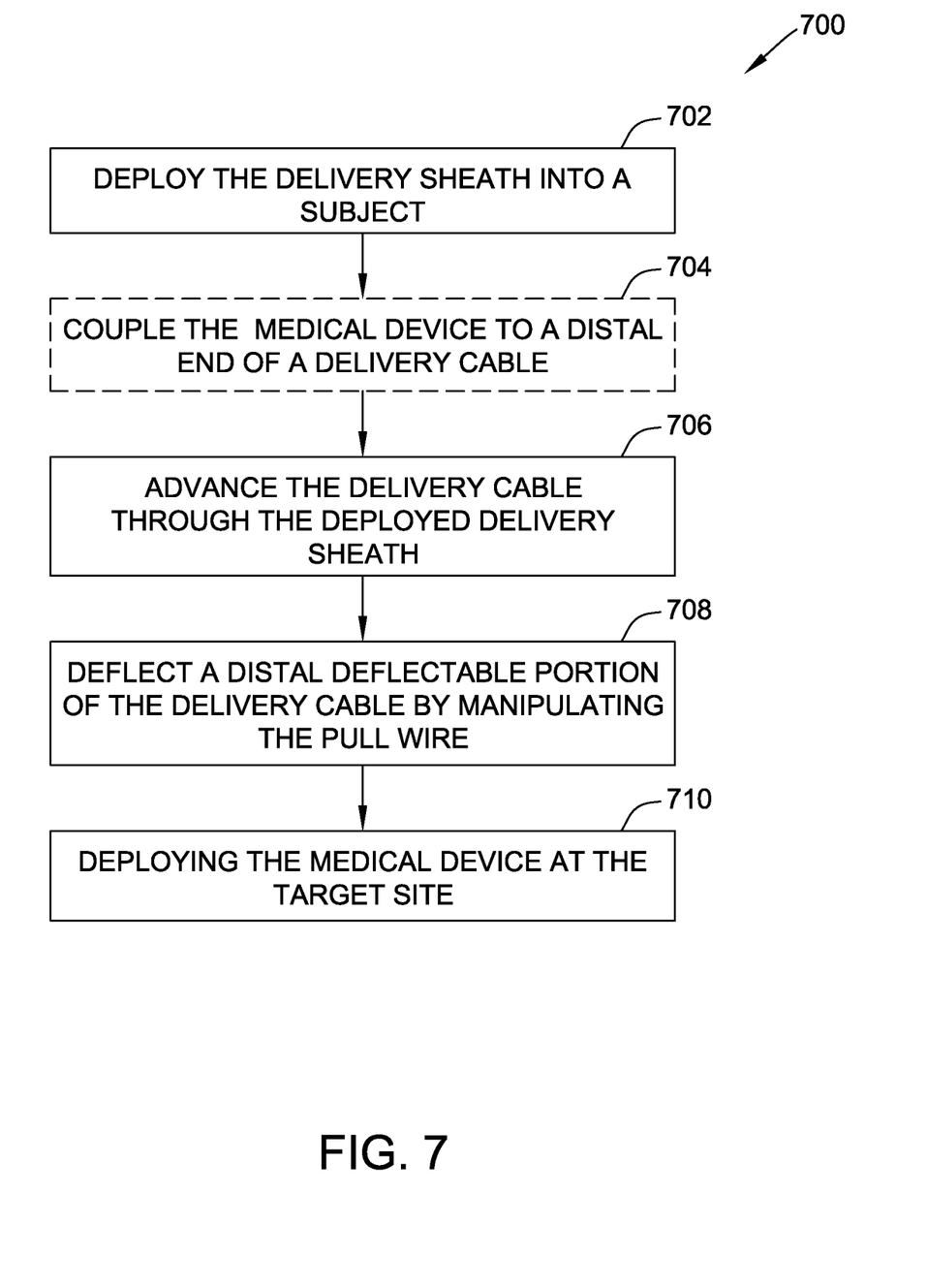
FIG. 7 is a flow diagram of a method for implanting a medical device at a target site according to one embodiment.

FIG. 7 is a flow diagram of a method 700 for implanting a medical device (e.g., collapsible occluder) at a target site in a subject using a delivery cable and a delivery sheath, such as the delivery cable 200 and the delivery sheath 204 (both shown in FIG. 2), according to one embodiment. Notably, the steps in method 700 may be performed in any suitable order, and are not limited to being performed in the order shown in FIG. 7.

Method 700 includes deploying 702 the delivery sheath into the subject. In some embodiments, the medical device is already attached to a distal end of the delivery cable in a "preloaded" configuration. Alternatively, in other embodiments, method 700 may optionally include coupling 704 the medical device to a distal end of the delivery cable. As described above, the delivery cable includes at least a flexible inner core, an outer coil surrounding at least a portion of the flexible inner core, and a pull wire disposed between the flexible inner core and the outer coil. Method 700 further includes advancing 706 the delivery cable through the deployed delivery sheath, for example, until the medical device exits the delivery sheath and reaches the target site. Method 700 further includes deflecting 708 a distal deflectable portion of the delivery cable by manipulating the pull wire, and deploying 710 the medical device at the target site by detaching the medical device from the delivery cable. In some embodiments, detaching the medical device from the delivery cable includes rotating the flexible inner core relative to the outer coil.

Although a number embodiments of this disclosure have been described above with a certain degree of particularity, those skilled in the art could make numerous alterations to the disclosed embodiments without departing from the spirit or scope of the disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A delivery cable for delivering a medical device, the delivery cable comprising:
    a flexible inner core;
    an outer coil coaxial with and surrounding at least a portion of the flexible inner core, wherein the flexible inner core is rotatable within and relative to the outer coil;
    a pull wire disposed between the flexible inner core and the outer coil, the pull wire configured to deflect a distal deflectable portion of the delivery cable upon manipulation thereof; and
    an endscrew coupled to a distal end of the flexible inner core and configured to engage the medical device, wherein the endscrew includes a threaded portion for engaging the medical device.

2. The delivery cable of claim 1, wherein the pull wire is coupled to the outer coil.

3. The delivery cable of claim 1, wherein rotation of the flexible inner core causes corresponding rotation of the endscrew to disengage the endscrew from the medical device.

4. The delivery cable of claim 3, further comprising a bushing coupled between a proximal portion of the endscrew and the outer coil to provide a bearing interface between the endscrew and the outer coil.

5. The delivery cable of claim 4, wherein the pull wire is coupled to the outer coil via the bushing.

6. The delivery cable of claim 4, wherein the bushing is coupled to an inner surface of the outer coil.

7. The delivery cable of claim 4, further comprising a proximal disc coupled to a proximal end of the endscrew, the proximal disc configured to prevent proximal translation of the bushing within the outer coil.

8. A delivery device for delivering a medical device to a target site, the delivery device comprising:
    an outer sheath; and
    a delivery cable positioned within the outer sheath and movable along a longitudinal axis with respect to the outer sheath, the delivery cable comprising:
        a flexible inner core;
        an outer coil coaxial with and surrounding at least a portion of the flexible inner core, wherein the flexible inner core is rotatable within and relative to the outer coil;
        a pull wire disposed between the flexible inner core and the outer coil, the pull wire configured to deflect a distal deflectable portion of the delivery cable upon manipulation thereof; and
        an endscrew coupled to a distal end of the flexible inner core and configured to engage the medical device, wherein the endscrew includes a threaded portion for engaging the medical device.

9. The delivery device of claim 8, further comprising a handle assembly coupled to a proximal end of the delivery cable, wherein the handle assembly comprises a deflection control coupled to a proximal end of the pull wire, wherein manipulation of the deflection control increases tension in the pull wire to deflect the distal deflectable portion of the delivery cable.

10. The delivery device of claim 9, further comprising a handle assembly coupled to a proximal end of the delivery cable, wherein the handle assembly includes a rotation control coupled to a proximal end of the flexible inner core, wherein manipulation of the rotation control causes rotation of the flexible inner core and corresponding rotation of the endscrew to disengage the endscrew from the medical device.

11. The delivery device of claim 10, further comprising a bushing coupled between a proximal portion of the endscrew and the outer coil to provide a bearing interface between the endscrew and the outer coil.

12. A method of manufacturing a delivery cable, the method comprising:
    providing a flexible inner core;
    inserting the flexible inner core at least partially into an outer coil such that the flexible inner core is coaxial with the outer coil, wherein the flexible inner core is rotatable within and relative to the outer coil;
    coupling an endscrew to a distal end of the flexible inner core;
    inserting a pull wire between the flexible inner core and the outer coil; and
    coupling the pull wire to the outer coil.

13. The method of claim 12, further comprising coupling a bushing between a proximal portion of the endscrew and the outer coil to provide a bearing interface between the endscrew and the outer coil.

14. The method of claim 13, further comprising coupling a proximal disc to a proximal end of the endscrew, the proximal disc configured to prevent proximal translation of the bushing within the outer coil.

15. The method of claim 13, wherein the coupling of the pull wire to the outer coil comprises:
    coupling the pull wire to the bushing; and
    coupling the bushing to the outer coil.

16. The method of claim 12, further comprising:
    coupling a handle assembly to a proximal end of the delivery cable, wherein the handle assembly includes a rotation control; and
    coupling a proximal end of the flexible inner core to the rotation control for rotation of the flexible inner core relative to the outer coil.

17. The method of claim 12, further comprising:
    coupling a handle assembly to a proximal end of the delivery cable, wherein the handle assembly includes a deflection control; and
    coupling a proximal end of the pull wire to the deflection control.

* * * * *